United States Patent
Cao et al.

(10) Patent No.: US 11,439,782 B2
(45) Date of Patent: Sep. 13, 2022

(54) INFLATABLE LARYNGEAL MASK AIRWAY FOR ENDOSCOPIC DIAGNOSIS AND TREATMENT

(71) Applicant: ZHEJIANG JENSTON MEDICAL TECHNOLOGY CO., LTD., Huzhou (CN)

(72) Inventors: Zan Cao, Huzhou (CN); Feng Deng, Huzhou (CN); Fan Li, Huzhou (CN)

(73) Assignee: ZHEJIANG JENSTON MEDICAL TECHNOLOGY CO., LTD., Huzhou (CN)

( * ) Notice: Subject to any disclaimer, the term of this patent is extended or adjusted under 35 U.S.C. 154(b) by 310 days.

(21) Appl. No.: 16/744,355

(22) Filed: Jan. 16, 2020

(65) Prior Publication Data
US 2020/0230339 A1 Jul. 23, 2020

(30) Foreign Application Priority Data
Jan. 18, 2019 (CN) .......................... 201910046357.6

(51) Int. Cl.
*A61M 16/04* (2006.01)
*A61M 16/06* (2006.01)

(52) U.S. Cl.
CPC .......... *A61M 16/045* (2014.02); *A61M 16/06* (2013.01)

(58) Field of Classification Search
CPC .......... A61M 16/0434; A61M 16/0415; A61M 16/0486; A61M 16/0488; A61M 16/0409; A61M 16/0009; A61M 16/0402; A61B 1/267
See application file for complete search history.

(56) References Cited

U.S. PATENT DOCUMENTS

| | | | | |
|---|---|---|---|---|
| 2008/0276932 A1* | 11/2008 | Bassoul | ............ | A61M 16/0463 128/200.26 |
| 2011/0040211 A1* | 2/2011 | Addington | ........... | A61B 5/4884 600/587 |
| 2012/0174929 A1* | 7/2012 | Esnouf | .............. | A61M 16/0409 128/207.15 |
| 2014/0323806 A1* | 10/2014 | Brain | ................... | A61B 1/2733 600/115 |

(Continued)

FOREIGN PATENT DOCUMENTS

CN 202951869 U 5/2013

*Primary Examiner* — Colin W Stuart
*Assistant Examiner* — Douglas Y Sul
(74) *Attorney, Agent, or Firm* — Bacon & Thomas, PLLC

(57) ABSTRACT

The present invention provides an inflatable laryngeal mask airway (LMA) for endoscopic diagnosis and treatment. The inflatable LMA for endoscopic diagnosis and treatment includes a cuff and an airway tube. The cuff is fixedly connected to the airway tube. The airway tube includes a ventilation airway, an endoscope channel and an inflation channel which are arranged in parallel. The ventilation inlet, the endoscope inlet and the inflation inlet are located at the end of the airway tube away from the cuff. The cuff includes a base body and an air bag connected to the base body. The inflation outlet is connected to the air bag. The endoscope outlet is connected to a lower surface of the base body and directed to the front side of the base body. The back surface of the endoscope channel is provided with an expansion port extending from the endoscope inlet to the endoscope outlet.

9 Claims, 3 Drawing Sheets

(56) References Cited

U.S. PATENT DOCUMENTS

| | | | |
|---|---|---|---|
| 2016/0008562 A1* | 1/2016 | Sagales Manas | A61M 16/04 600/109 |
| 2016/0101254 A1* | 4/2016 | Hansen | A61M 16/0445 128/207.15 |
| 2016/0206841 A1* | 7/2016 | Vadivelu | A61M 16/0463 |
| 2016/0262603 A1* | 9/2016 | Molnar | A61B 1/233 |
| 2016/0346493 A1* | 12/2016 | Wight | A61M 16/0445 |
| 2017/0209022 A1* | 7/2017 | Molnar | A61M 16/0461 |
| 2018/0169365 A1* | 6/2018 | Sawyer | A61M 16/0488 |
| 2018/0339121 A1* | 11/2018 | Ootake | A61M 16/024 |

\* cited by examiner

INFLATABLE LARYNGEAL MASK AIRWAY FOR ENDOSCOPIC DIAGNOSIS AND TREATMENT

TECHNICAL FIELD

The present invention relates to the technical field of medical instruments, and in particular to an inflatable laryngeal mask airway (LMA) for endoscopic diagnosis and treatment.

BACKGROUND

The Chinese invention patent with the publication number CN202951869U discloses a laryngeal mask airway (LMA) for painless gastroscope diagnosis and treatment. The LMA includes a cuff, an airway tube. The cuff is fixedly connected to the airway tube. The LMA can reduce damage to the mucosa of a patient and improve the medical effect by the inflatable cuff.

At present, the sizes of the existing gastroscopes/bronchofiberscopes/esophagoscopes on the market are different. For example, the esophagoscope has a diameter of 17 mm, and a length at the end of a hard tube greater than 40 mm. Therefore, an LMA for diagnosis and treatment similar to that described above has a limited application. On one hand, the painless gastroscope has an extremely tube, such that the gastroscope or bronchofiberscope or esophagoscope cannot enter the tube; and on the other hand, the gastroscope or bronchofiberscope or esophagoscope can enter the tube that has a transitional radian, the gastroscope or bronchofiberscope or esophagoscope is stuck in the tube and cannot move. The LMA will be damaged if it is inserted with a brute force. At the same time, in emergency situations such as first aid, replacing by an LMA of a different size or choosing an LMA of the incorrect size will cause serious consequences such as missing the best treatment time.

SUMMARY

An objective of the present invention is to provide an inflatable laryngeal mask airway (LMA) for endoscopic diagnosis and treatment, thereby solving the problems in the prior art.

To achieve the objective of the present invention, the present invention adopts the following technical solutions.

An inflatable LMA for endoscopic diagnosis and treatment includes a cuff and an airway tube. The cuff is fixedly connected to the airway tube. The airway tube includes a ventilation airway, an endoscope channel and an inflation channel which are arranged in parallel. The ventilation airway includes a ventilation inlet and a ventilation outlet. The endoscope channel includes an endoscope inlet and an endoscope outlet. The inflation channel includes an inflation inlet and an inflation outlet. The ventilation inlet, the endoscope inlet and the inflation inlet are located at the end of the airway tube away from the cuff. The cuff includes a base body and an air bag connected to the base body. The air bag surrounds the edge of the base body in an annular shape. The inflation outlet is connected to the air bag. The endoscope outlet is connected to a lower surface of the base body and directed to the front side of the base body. The back surface of the endoscope channel is provided with an expansion port extending from the endoscope inlet to the endoscope outlet. The air bag is easily tapered from the rear side to the front side of the base body.

As a preference of the present invention, the ventilation outlet penetrates upward from the lower surface of the base body to an upper surface of the base body.

As a preference of the present invention, the ventilation inlet is externally connected with a connecting end protruding from the end of the airway tube, and the connecting end inclines outwards away from the endoscope inlet.

As a preference of the present invention, the inflation inlet is a hose extending outward from the airway tube.

As a preference of the present invention, at the inflation inlet there is a one-way valve with the ventilation direction directed to the inflation outlet.

As a preference of the present invention, a pressure indicator is connected between the one-way valve and the inflation outlet.

As a preference of the present invention, the middle part of the airway tube is an arc transition, and the included angle of airway tube sections on both sides of the arc transition is 80-110°.

The inflatable LMA for endoscopic diagnosis and treatment according to claim 1 is characterized in that the end of the airway tube connecting to the cuff is tapered from the rear end to the front end of the base body.

As a preference of the present invention, the endoscope channel is internally provided with a plastic tube, and the side surface of the plastic tube is provided with an opening corresponding to the expansion port.

As a preference of the present invention, the plastic tube has an outward flanging at the endoscope inlet.

The beneficial effects of the present invention are:

1. By the expansion port, the airway tube can be varied as expanding from the expansion port to two sides of its opening when different endoscopes (especially larger endoscopes) enter the airway tube, so that the shape change is controllable and is convenient for removing, without causing any unexpected harm to a patient, and meanwhile the sealing of the throat can be completed just with a simple structure; and 2. the air bag that is inflated and can be controlled through the one-way valve and the pressure indicator, can control its inflation state through a pressure, so as to adapt to the physiological signs of the patient and reduce the compression on the throat of the patient.

where the items in the figures are respectively: 1 represents a cuff 11 represents a base body, 12 represents an air bag, 21 represents a ventilation inlet, 22 represents a ventilation outlet, 23 represents a connection end, 31 represents an endoscope inlet, 32 represents an endoscope outlet, 33 represents an expansion port, 34 represents a plastic tube, 35 represents a flanging, 41 represents an inflation inlet, 42 represents an inflation outlet, 43 represents a one-way valve, and 44 represents a pressure indicator.

DETAILED DESCRIPTION

The present invention is described in detail below with reference to the accompanying drawings.

Figure 1:
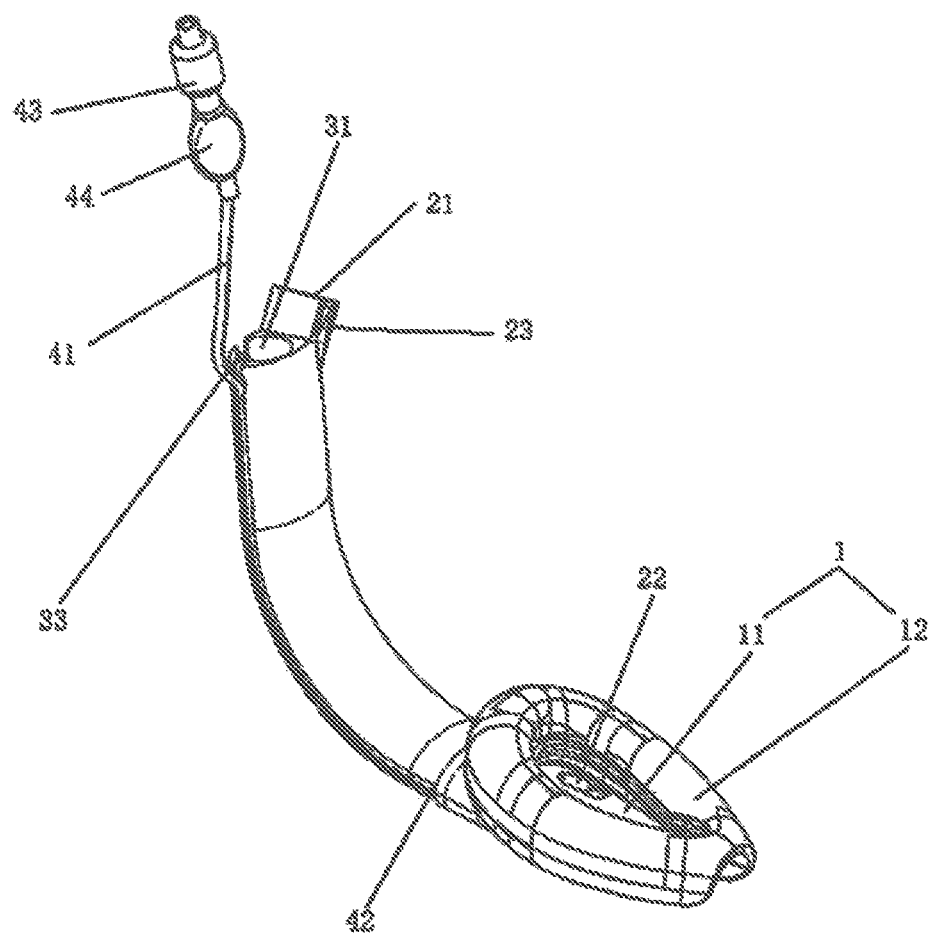
FIG. 1 is a three-dimensional schematic diagram of the present invention.
Figure 2:
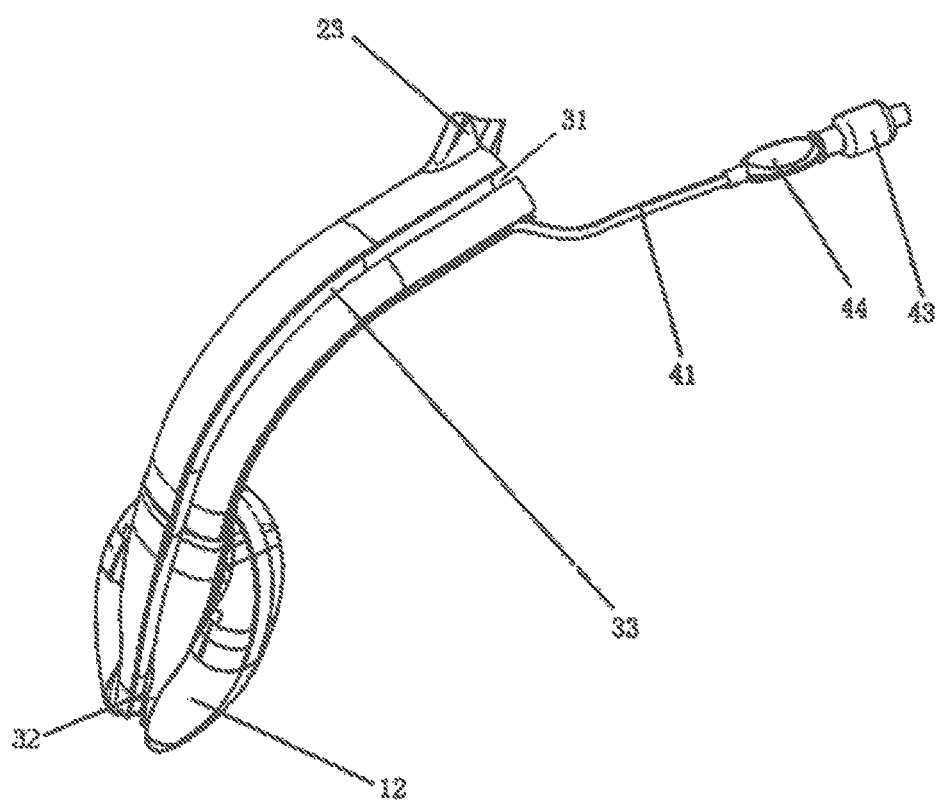
FIG. 2 is a three-dimensional schematic view of the back side of the cuff of the present invention.
Figure 3:
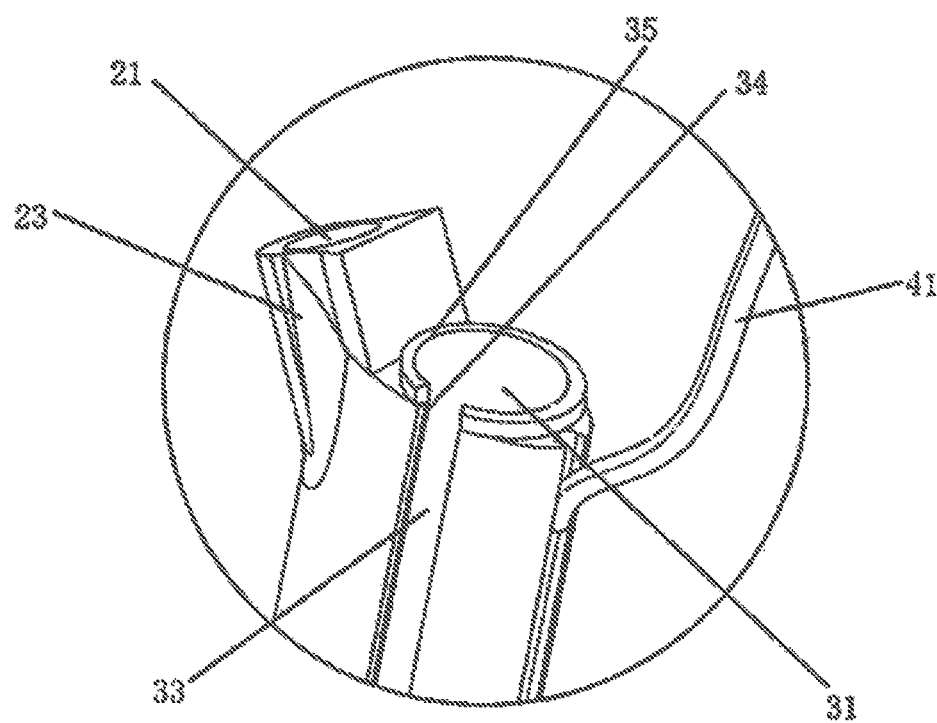
FIG. 3 is a schematic structural view of an endoscope inlet of the present invention.

As shown in FIGS. 1, 2 and 3, an inflatable LMA for endoscopic diagnosis and treatment includes a cuff 1 and an airway tube, wherein the cuff 1 is fixedly connected to the airway tube; the airway tube includes a ventilation airway, an endoscope channel and an inflation channel which are made of medical silica gel or similar materials and are arranged in parallel. The ventilation airway includes a ventilation inlet 21 and a ventilation outlet 22 at two ends. The endoscope channel includes an endoscope inlet 31 and an endoscope outlet 32 at two ends. The inflation channel includes an inflation inlet 41 and an inflation outlet 42 at two ends. The ventilation inlet 21, the endoscope inlet 31 and the inflation inlet 41 are positioned at one end of the airway tube away from the cuff 1. The cuff 1 includes a base body 11 made of silica gel and an air bag 12 connected to the base body 11. The air bag 12 surrounds the edge of the base body 11 in an annular shape. The inflation outlet 42 is connected to the air bag 12 for supplying air to the air bag 12. The endoscope outlet 32 is connected to a lower surface of the base body 11 and directed to the front side of the base body 11. The back surface of the endoscope channel is provided with an expansion port 33 extending from the endoscope inlet 31 to the endoscope outlet 32. The air bag 12 is tapered from the rear side to the front side of the base body 11. When in use, the cuff 1 is inserted into the throat of a patient, one end at the inlet of the airway tube is exposed from the mouth of the patient, and at this point the ventilation tube 2 is communicated with the outside and the trachea of the patient to provide breathing air for the patient; the endoscope channel is communicated with the outside and the esophagus of the patient for inserting an endoscope for examination, and meanwhile the inflation tube 4 is used to supply air to the air bag 12 to realize sealing of the throat and prevent backflow and overflow of gastric juice, saliva, etc. The interaction between the endoscope and the endoscope channel during insertion pushes the endoscope channel away from the expansion port 33 and enables the shape of the endoscope channel to change towards both sides, thereby realizing convenient passage and also causing damage to the device. The air bag 12, which tapered from back to front, enables that under the structure having the expansion port 33, the inflation at the front end of the air bag 12 not only realizes the original sealing effect, but also does not affect the entry and exit of the endoscope due to the smaller structure.

In this embodiment, a ventilation outlet 22 penetrates upward from the lower surface of the base body 11 to an upper surface of the base body 11. Therefore a smaller volume can be had for use during insertion.

In this embodiment, the ventilation inlet 21 is externally connected with a connection end 23 protruding from the end of the airway tube. The connection end 23 is used for connecting devices such as an external ventilator to provide oxygen for the patient. The connection end 23 is inclined outward away from the endoscope inlet 31, thereby making space there and avoiding blocking the endoscope from entering the space.

In this embodiment, the inflation inlet 41 is a hose extending outward from the airway tube, which can be conveniently inserted into an air supply device to supply air to the air bag 12. The stretchability and mobility of the hose enable the air supply device to be placed at a far place to provide space for entrance of the endoscope and use by an operator, and meanwhile also reduce the volume of the airway tube to prevent the throat of the patient from being squeezed.

In this embodiment, at the inflation inlet 41 there is a one-way valve 43 with the ventilation direction directed to the inflation outlet 42, and the one-way valve 43 is used for preventing sealing failure caused by reverse flowing out of the air from the air bag 12 under the action of being squeezed by the throat muscle of the patient.

In this embodiment, a pressure indicator 44 is connected between the one-way valve 43 and the inflation outlet 42. In this embodiment, the pressure indicator 44 is in the shape of an air bag, such that the inflation of it indicates the pressure state of the inner wall, prompting the operator and thus preventing the blood vessel from being squeezed by excessive air pressure.

In this embodiment, the middle part of the airway tube is an arc transition, and the included angle of airway tube sections on both sides of the arc transition is 80-110°. Therefore, on one hand, it can adapt to the throat structure of human body, and on the other hand, its angle can facilitate insertion of the endoscope.

In this embodiment, the end 23 of the airway tube connecting to the cuff 1 is tapered from the rear end to the front end of the base body 11 to realize convenient insertion.

In this embodiment, the endoscope channel is internally provided with a plastic tube 34, and the side surface of the plastic tube 34 is provided with an opening corresponding to the expansion port 33. The plastic tube 34 supports the endoscope channel by its relatively hard property, so as to prevent the endoscope channel from being pressed by the laryngeal pressure and thus prevent the endoscope insertion from being blocked. At the same time, it provides the function similar to a dental brace to prevent the patient's teeth from broken due to biting. At the same time, the elasticity of the plastic tube 34 also enables it to be conveniently expanded to facilitate insertion of the endoscope.

In this embodiment, the plastic tube 34 has an outward flanging 35 at the endoscope inlet 31, and this upward flanging 35 can guide the insertion of the endoscope.

The embodiments described above are only intended to describe the preferred embodiments of the present invention, rather than limiting the concept and scope of the present invention. Various modifications and improvements performed on the technical solution of the present invention by those of ordinary skills in the art without departing from the design concept of the present invention shall fall within the claimed scope of the present invention. The technical content claimed by the present invention has been fully recorded in the Claims.

What is claimed is:

1. An inflatable laryngeal mask airway (LMA) for endoscopic diagnosis and treatment, comprising a cuff (1) and an airway tube, wherein the cuff (1) is fixedly connected to the airway tube; the airway tube comprises a ventilation airway, an endoscope channel and an inflation channel which are arranged in parallel; the ventilation airway comprises an ventilation inlet (21) and an ventilation outlet (22); the endoscope channel comprises an endoscope inlet (31) and an endoscope outlet (32); the inflation channel comprise an inflation inlet (41) and an inflation outlet (42), the ventilation inlet (21), the endoscope inlet (31) and the inflation inlet (41) are located at one end of the airway tube away from the cuff (1), the cuff (1) comprises a base body (11) and an air bag (12) connected to the base body (11), and the air bag (12) surrounds an edge of the base body (11) in an annular shape, the inflation outlet (42) is connected to the air bag (12), the endoscope outlet (32) is connected to a lower surface of the base body (11) and directed to a front side of the base body (11), and wherein a back surface of the endoscope channel is provided with an expansion port (33) extending from the endoscope inlet (31) to the endoscope outlet (32), the expansion port (33) penetrates through a side wall of the endoscope channel so that a shape of the endoscope channel is changeable during insertion of an endoscope into the endoscope channel, and the air bag (12) is tapered from a rear side to the front side of the base body (11); wherein the endoscope channel is internally provided with a plastic tube (34), and a side surface of the plastic tube (34) is provided with an opening corresponding to the expansion port (33).

2. The inflatable LMA for endoscopic diagnosis and treatment according to claim 1, wherein the ventilation outlet (22) penetrates upward from the lower surface of the base body (11) to an upper surface of the base body (11).

3. The inflatable LMA for endoscopic diagnosis and treatment according to claim 1, wherein the ventilation inlet (21) is externally connected with a connecting end (23) protruding from the end of the airway tube, and the connecting end (23) inclines outwards away from the endoscope inlet (31).

4. The inflatable LMA for endoscopic diagnosis and treatment according to claim 1, wherein the inflation inlet (41) is a hose extending outward from the airway tube.

5. The inflatable LMA for endoscopic diagnosis and treatment according to claim 4, wherein at the inflation inlet (41) there is a one-way valve (43) with a flow direction directed to the inflation outlet (42).

6. The inflatable LMA for endoscopic diagnosis and treatment according to claim 5, wherein a pressure indicator (44) is connected between the one-way valve (43) and the inflation outlet (42).

7. The inflatable LMA for endoscopic diagnosis and treatment according to claim 1, wherein a middle part of the airway tube is an arc transition, and an included angle of airway tube sections on both sides of the arc transition is 80-110°.

8. The inflatable LMA for endoscopic diagnosis and treatment according to claim 1, wherein an end (23) of the airway tube connecting to the cuff (1) is tapered from the rear side to the front side of the base body (11).

9. The inflatable LMA for endoscopic diagnosis and treatment according to claim 1, wherein the plastic tube (34) has an outward flanging (35) at the endoscope inlet (31).

* * * * *